(12) United States Patent
Miyagi et al.

(10) Patent No.: US 8,066,722 B2
(45) Date of Patent: Nov. 29, 2011

(54) CLIP APPLIER

(75) Inventors: Kunihiko Miyagi, Tokyo (JP);
Masayuki Misawa, Tokyo (JP)

(73) Assignee: Machida Endoscope Co., Ltd., Bunkyo-Ku, Tokyo (JP)

( * ) Notice: Subject to any disclaimer, the term of this patent is extended or adjusted under 35 U.S.C. 154(b) by 672 days.

(21) Appl. No.: 12/238,907

(22) Filed: Sep. 26, 2008

(65) Prior Publication Data
US 2009/0088777 A1    Apr. 2, 2009

(30) Foreign Application Priority Data

Sep. 27, 2007 (JP) ................... 2007-250558

(51) Int. Cl.
*A61B 17/04* (2006.01)
(52) U.S. Cl. ....................................................... 606/142
(58) Field of Classification Search .................. 606/142, 606/151, 157, 158, 219; 600/104; 227/176.1
See application file for complete search history.

(56) References Cited

U.S. PATENT DOCUMENTS

| | | | |
|---|---|---|---|
| 3,827,438 A | 8/1974 | Kees, Jr. | |
| 4,038,987 A | 8/1977 | Komiya | |
| 4,444,187 A * | 4/1984 | Perlin | ............................ 606/158 |
| 4,484,581 A * | 11/1984 | Martin et al. | .................. 606/158 |
| 4,602,631 A | 7/1986 | Funatsu | |
| 4,706,668 A | 11/1987 | Backer | |
| 5,049,153 A * | 9/1991 | Nakao et al. | .................. 606/151 |
| 6,099,536 A * | 8/2000 | Petillo | ............................ 606/142 |

FOREIGN PATENT DOCUMENTS

| | | |
|---|---|---|
| JP | 07041447 | 10/1995 |
| WO | 9713466 A | 4/1997 |

OTHER PUBLICATIONS

European Search Report for related Application No. 08253090.8.

* cited by examiner

*Primary Examiner* — Melanie Tyson
*Assistant Examiner* — Son Dang
(74) *Attorney, Agent, or Firm* — Stephen B. Salai, Esq.; Thomas B. Ryan, Patent Agent; Harter Secrest & Emery LLP (57) ABSTRACT

A clip applier includes a body 21, an insertion tube 22 extending from the body 21 and inserted in a channel of an endoscope and a clamp mechanism 24 disposed at a distal end of the insertion tube 22. The clamp mechanism 24 has a support member 28 fixed at the distal end of the insertion tube 22 and a pair of clamp members 30 rotatably supported by the support member 28. The clamp members 30 are connected to a distal end of a wire 25 via a pair of links 35. The clamp members 30 respectively include gripping portions 32 protruding form the support member 28. A clip 50 is received in receiving grooves 32a of the gripping portions 32. When the wire 25 is pulled by operating an operation member disposed on the body 21, the clamp members 30 are rotated against an elastic force of a hinge portion 51 of the clip 50, thereby causing a pair of clip portions 53 of the clip 50 to be opened.

7 Claims, 5 Drawing Sheets

CLIP APPLIER

BACKGROUND OF THE INVENTION

This invention relates to a clip applier for use in brain surgery, etc.

To prevent rupture of an aneurysm in the brain, for example, an operative treatment is performed in which a neck of the aneurysm is ligated with a clip to block the communication between the aneurysm and the blood vessel.

A clip used in the operation integrally includes a hinge portion, a pair of clip portions and a pair of connecting portions respectively connecting opposite ends of the hinge portion to the pair of clip portions. The connecting portions intersect with each other. The pair of clip portions are biased to be closed by an elastic force of the hinge portion.

In the operation, a cranium is widely opened and the clip is applied to an affected area, e.g. the neck of the aneurysm, using a tweezers-like instrument while the affected area is being observed with a microscope. As shown in Japanese Utility Model Publication No. H7-41447, the instrument includes receiving recesses at distal end portions of a pair of grip portions. The clip is held by the instrument with the pair of connecting portions of the clip received in the receiving recesses and the pair of clip portions of the clip protruding from distal ends of the tweezers-like instrument. The clip portions of the clip are opened by pressing the pair of the connecting portions against the elastic force of the hinge portion. With the affected area placed between the clip portions, the pressing force is released, thereby ligating the affected area with the pair of clip portions.

However, in the above mentioned operation, it is required to widely open the cranium, which tends to cause a heavy burden on a patient.

SUMMARY OF THE INVENTION

In order to solve the above mentioned problem, the present invention provides a clip applier for applying a clip to an affected area to ligate the affected area, the clip integrally including a hinge portion, a pair of clip portions and a pair of connecting portions respectively connecting opposite ends of the hinge portion to the pair of clip portions, the connecting portions intersecting with each other, the pair of clip portions being biased to be closed by an elastic force of the hinge portion, characterized in that the clip applier includes: an applier body; an insertion tube extending from the applier body and inserted through a channel of an endoscope; a clamp mechanism disposed at a distal end of the insertion tube; an operation member disposed on the applier body; and a wire passing through the insertion tube to connect the clamp mechanism and the operation member, the clamp mechanism including a support member fixed at the distal end of the insertion tube and a pair of clamp members supported by the support member, at least one of the clamp members being rotatable with respect to the support member, the pair of clamp members respectively including gripping portions protruded from the support member, the gripping portions respectively including receiving grooves in surfaces of the gripping portions facing each other, the pair of connecting portions of the clip respectively received in the receiving grooves of the gripping portions of the clamp members and the clip portions of the clip protruded from the gripping portions in a condition where the clip is held by the clamp members, the at least one of the clamp members being connected to the operation member via the wire, when the wire is pulled by operating the operation member, the at least one of the clamp members being rotated against the elastic force of the hinge portion of the clip, thereby causing the gripping portions of the pair of clamp members to press the pair of connecting portions of the clip, thereby opening the clip portions.

In the above mentioned arrangement, when the clip applier is inserted through the endoscope, the clip can be applied to the affected area while being observed with the endoscope. This allows a ligation to be performed without widely opening the body of a patient. The clip applier also allows the pair of clip portions of the clip to be smoothly opened by a wire drawing operation. When the operating force is released with the affected area placed between the opened clip portions, the pair of clip portions are closed by the elastic force of the hinge portion of the clip, surely ligating the affected portion.

Preferably, the insertion tube includes a hard portion to be rigidly joined with the applier body and a flexible portion having a greater length than the hard portion.

In this arrangement, when the clip applier is inserted through a flexible endoscope, the applier body can be held in a stable posture with respect to the endoscope by clamping and fixing the hard portion with a clamping means provided in the endoscope. This eliminates the necessity of manpower for holding the applier body.

Preferably, distal edge portions of the gripping portions of the clamp members serve as pressing portions for pressing the connecting portions of the clip.

In this arrangement, the clip portions can be opened with a smaller operating force since the connecting portions of the clip are pressed at points relatively distanced from the hinge portion.

Preferably, each of the pair of clamp members is abutted against the connecting portion of the clip at two points when the clamp members hold the clip, one point being in the distal edge portion of the gripping portion and the other point being in a bottom surface of the receiving groove.

In this arrangement, the clip can be stably held.

Preferably, the pair of clamp members intersect with each other, the clamp members being supported by the support member at the intersecting portions of the clamp members such that the clamp members are rotatable about a common shaft, the clamp members respectively including link portions integrally formed with the gripping portions, the clamp mechanism further including a pair of links, one ends of the links being respectively rotatably connected to the link portions of the clamp members, the other ends of the links being rotatably connected to the distal end of the wire, the link portions of the pair of clamp members and the pair of links constituting a pantograph-type link mechanism, the pair of clamp members being rotated via the link mechanism by pulling the wire, thereby opening the clip portions of the clip.

In this arrangement, a pulling force of the wire can be smoothly and securely transmitted to the clamp members by the link mechanism.

Preferably, a length of the link portions of the pair of clamp members is greater than a length of the pair of links.

In this arrangement, the clip can be opened with a smaller operating force.

Preferably, the support member includes a base portion fixed to the distal end of the insertion tube and a pair of support pieces extending from the base portion, the link portions of the clamp members and the links being received between the support pieces, the clamp members rotatably supported at distal end portions of the support pieces, a dimension between opposite side surfaces of the gripping portions of each of the clamp members in a direction of a rotation axis being smaller than a dimension between outer surfaces of the pair of support pieces in the same direction, thereby forming steps between the outer surfaces of the support pieces and the side surfaces of the gripping portions of the clamp members.

This allows the clip to be observed without being obstructed by the gripping portions of the clamp members in a field of view of the endoscope, further facilitating smooth conduct of the operation.

Preferably, a spring is disposed in the applier body, the spring biasing the wire in a direction to pull the wire, an elastic force of the spring being smaller than the elastic force of the hinge portion of the clip.

In this arrangement, the force of the spring enables the pair of gripping portions of the clamp members to hold the clip stably.

In the another aspect of the present invention, there is provided a surgical assembly comprising an endoscope having a channel and a clip applier for applying a clip to an affected area to ligate the affected area, the clip integrally comprising a hinge portion, a pair of clip portions and a pair of connecting portions respectively connecting opposite ends of the hinge portion to the pair of clip portions, the connecting portions intersecting with each other, the pair of clip portions being biased to be closed by an elastic force of the hinge portion, wherein the clip applier comprises: an applier body; an insertion tube extending from the applier body and inserted through the channel of the endoscope; a clamp mechanism disposed at a distal end of the insertion tube; an operation member disposed on the applier body; and a wire passing through the insertion tube to connect the clamp mechanism and the operation member, the clamp mechanism comprising a support member fixed at the distal end of the insertion tube and a pair of clamp members supported by the support member, at least one of the clamp members being rotatable with respect to the support member, the pair of clamp members respectively comprising gripping portions protruded from the support member, the gripping portions respectively comprising receiving grooves in surfaces of the gripping portions facing each other, the pair of connecting portions of the clip respectively received in the receiving grooves of the gripping portions of the clamp members and the clip portions of the clip protruded from the gripping portions in a condition where the clip is held by the clamp members, the at least one of the clamp members being connected to the operation member via the wire, when the wire is pulled by operating the operation member, the at least one of the clamp members being rotated against the elastic force of the hinge portion of the clip, thereby causing the gripping portions of the pair of clamp members to press the pair of connecting portions of the clip, thereby opening the clip portions.

BRIEF DESCRIPTION OF THE DRAWINGS

FIG. 3A is a side view; FIG. 3B is a plan view; and FIG. 3C is a view from the distal end.

FIG. 4A to FIG. 4D are enlarged cross-sectional views of the distal end portion of the clip applier: FIG. 4A shows the clip applier in a natural state; FIG. 4B shows the clip applier with clamp members widely opened to grip a clip; FIG. 4C shows the clip applier gripping the clip; and FIG. 4D shows the clip applier with the clip elastically deformed and opened by the clamp members.

FIG. 5A and FIG. 5B are enlarged cross-sectional views of a distal end portion of a clip applier according to another embodiment of the present invention: FIG. 5A shows the clip applier in a natural state; and FIG. 5B shows the clip applier with the clip elastically deformed and opened by the clamp members.

DESCRIPTION OF THE REFERENCE NUMERALS

10 endoscope
20 clip applier
21 applier body
22 insertion tube
22a hard portion
22b flexible portion
23 operation member
24 clamp mechanism
27 compression coil spring (spring)
28 support member
30 clamp member
31 link portion
32 gripping portion
32a receiving groove
32x distal edge portion (pressing portion)
33 shaft
35 link
36, 37 shaft
40 link mechanism (link means)
50 clip
51 hinge portion
52 connecting portion
53 clip portion

DETAILED DESCRIPTION OF THE INVENTION

A clip applier for use with an endoscope according to a first embodiment of the present invention will now be described with reference to FIGS. 1 to 4.

Figure 1:
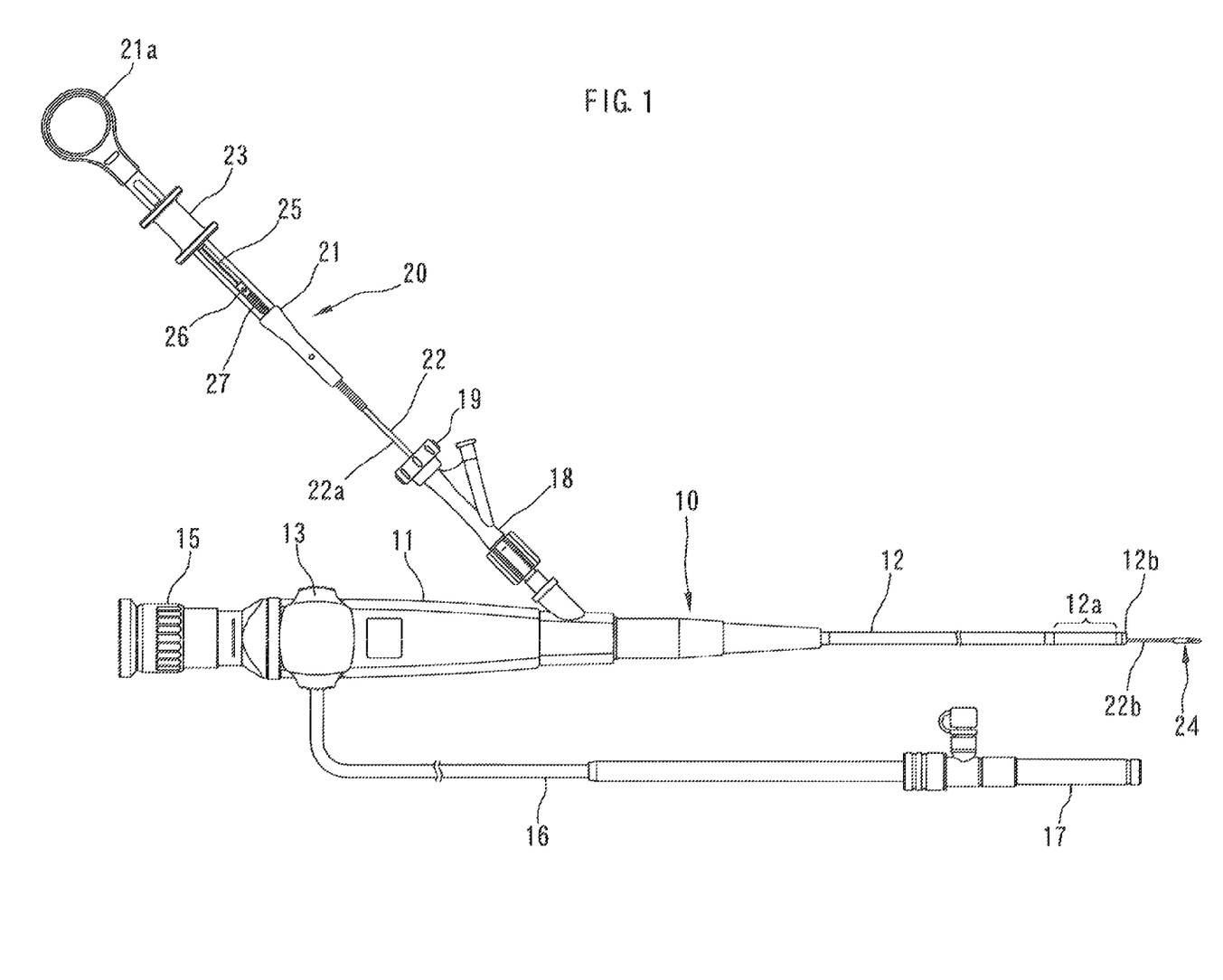
FIG. 1 is a side view of a clip applier and an endoscope according to a first embodiment of the present invention.

FIG. 1 shows an endoscope for brain surgery 10 and a clip applier 20 to be used with the endoscope 10.

The endoscope 10 will be described first. The endoscope 10 includes an elongated endoscope body 11 and a long flexible insertion portion 12 extending from a distal end of the body 11. The insertion portion 12 includes a bendable portion 12a extending a predetermined length form a distal end of the insertion portion 12. The bendable portion 12a can be bent by operating an operation portion 13 disposed on the body 11.

The insertion portion 12 further includes a hard tip 12b fixed at a distal end of the bendable portion 12a. An objective optical system (not shown) is received in the tip 12b adjacent to an observation window formed in an end surface of the tip 12b.

An ocular portion 15 having a built-in ocular optical system therein is mounted on a rear end of the body 11. The objective optical system and the ocular optical system are optically connected by a bundle of optical fibers (not shown) extending through the insertion portion 12 and the body 11. This enables images in a field of view of the objective optical system to reach the ocular optical system.

In this embodiment, a video camera can be connected to the ocular portion so that images from the objective optical system can be displayed on a television set connected to the video camera. Alternatively, light receiving elements may be disposed adjacent to the objective optical system so that the images from the objective optical system can be received by the light receiving elements, and electrical signals from the light receiving elements can be transmitted to the television set.

A light guide cable 16 is connected to the body 11. A light receiving portion 17 is mounted on a distal end of the light guide cable 16. On the other hand, an illumination optical system (not shown) is received in the tip 12b adjacent to an illumination window formed in the end surface of the tip 12b. The illumination optical system is optically connected to the light receiving portion 17 by another bundle of optical fibers (not shown) extending through the light guide cable 16, the body 11 and the insertion portion 12. This enables illumination light from an illumination generating device to be received by the light receiving portion 17, transmitted to the illumination optical system via the bundle of optical fibers and provided to an affected area through the illumination window.

A guide tube 18 is mounted to the body 11 such that the guide tube 18 is inclined with respect to an axis of the body 11. An interior space of the guide tube 18 continues to a channel formed in the body 11 and the insertion portion 12. The channel opens at the distal end surface of the tip 12b. A clamping dial 19 (clamping means) is mounted on an entrance end of the guide tube 18.

Arrangements are made such that the clip applier 20 can be inserted from the guide tube 18 through the channel until a distal end portion of the clip applier 20 is protruded from the distal end tip 12b. In FIG. 1, the clip applier 20 is shown with the distal end portion thereof protruded further than in a real surgical situation.

Figure 2:
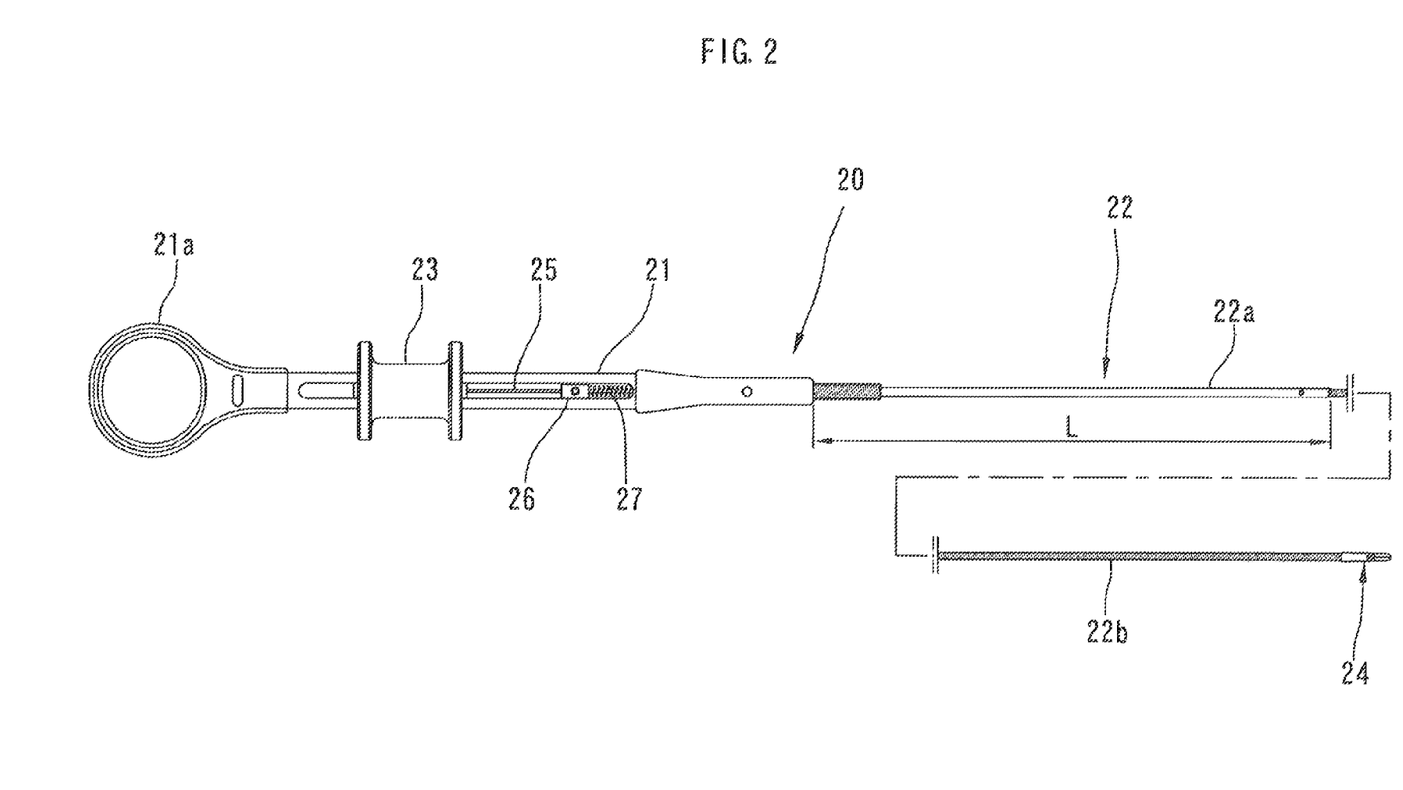
FIG. 2 is a side view of the clip applier.

As shown in FIGS. 1 and 2, the clip applier 20 includes an elongated applier body 21 and a long insertion tube 22 extending from a distal end of the body 21. A ring portion 21a (finger receiving portion) for receiving the thumb therein is provided on a rear end of the body 21. An operation member 23 having a tubular shape is mounted to the body 21 such that the operation member 23 is slidable in a longitudinal direction of the body 21.

The insertion tube 22 includes a hard portion 22a extending a predetermined length L from a distal end of the body 21 and a flexible portion 22b having a much greater length than the hard portion 22a. A clamp mechanism 24 is provided at a distal end of the flexible portion 22b.

The clip applier 20 further includes a wire 25. A rear end of the wire 25 is fixed to the operation member 23. The wire 25 extends through the body 21 and the insertion tube 22, and a distal end of the wire 25 is connected to the clamp mechanism 24.

A spring receiving member 26 is fixed to a vicinity of the rear end of the wire 25. A compression coil spring 27 is wound around the wire 25 and is disposed between the spring receiving member 26 and a spring receiving surface (not shown) formed in the body 21. The wire 25 is constantly biased to be drawn toward the body 21 by an elastic force of the spring 27. The spring receiving member 26 is slidable in the body 21 in a longitudinal direction of the body 21 as the wire 25 moves.

A structure of the clamp mechanism 24 at the distal end of the clip applier 20 is described hereinafter with reference to FIGS. 3 and 4. The clamp mechanism 24 includes a support member 28, a pair of clamp members 30 rotatably supported by the support member 28 and a pair of links 35.

The support member 28 includes a base portion 28a having a columnar shape and fixed on the distal end of the insertion tube 22 and a pair of support pieces 28b extending from the base portion 28a in a same direction as the insertion tube 22 and facing each other.

Each of the pair of clamp members 30 integrally includes a link portion 31 and a gripping portion 32 extending forwardly from the link portion 31. The link portion 31 is in a form of a plate having a smaller width than the gripping portion 32 and is offset from a center line of the gripping portion 32 in a width direction thereof.

The link portions 31 of the pair of clamp members 30 are received between the pair of support pieces 28b and are rotatably supported by a common shaft 33 at distal end portions of the support pieces 28b with the link portions 31 intersecting with each other.

The gripping portions 32 of the pair of clamp members 30 are protruded from the support pieces 28b. The gripping portions 32 respectively include elongated receiving grooves 32a in respective flat surfaces of the gripping portions facing each other. Distal edge portions 32x of the gripping portions 32 serve as pressing portions as will be described later.

Figure 3A:
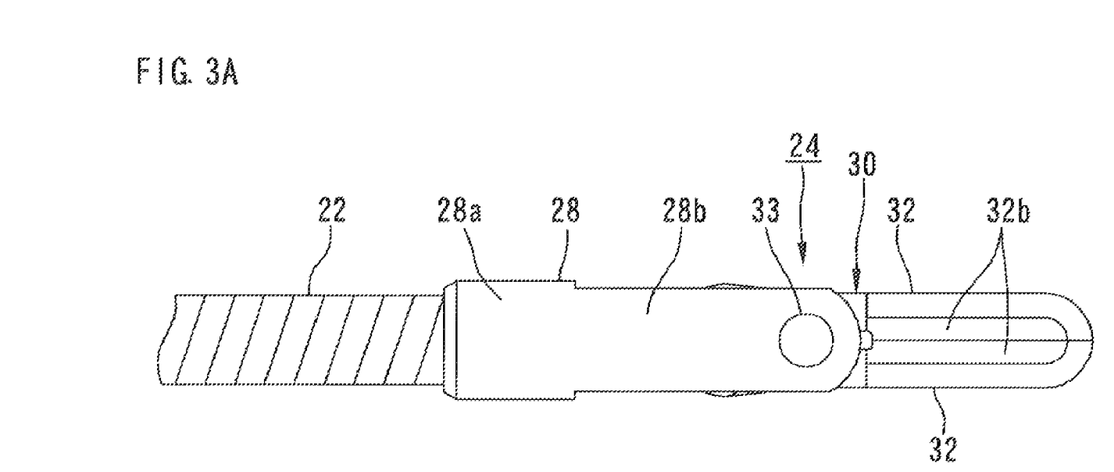
FIG. 3A to FIG. 3C are enlarged views of a distal end portion of the clip applier.
Figure 3B:
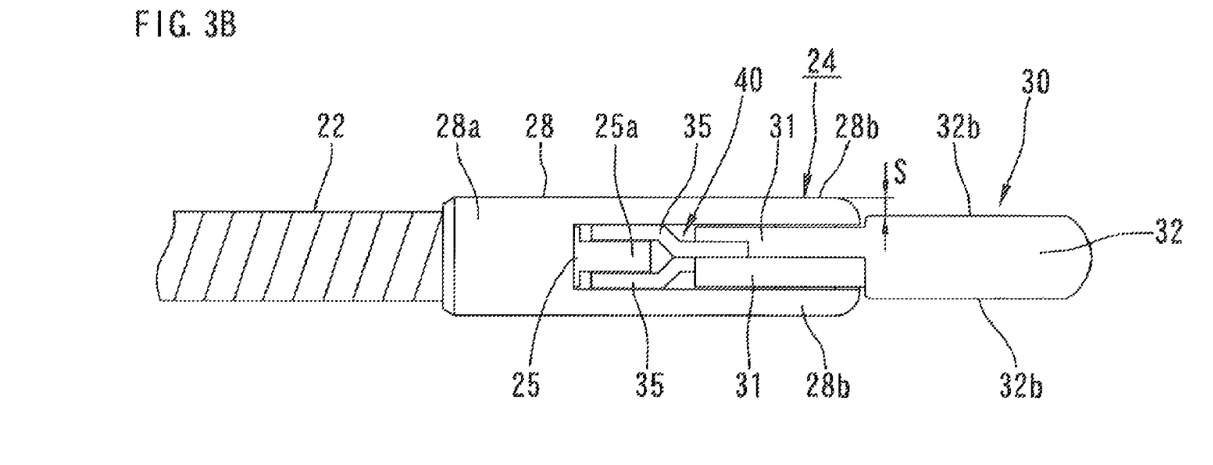
Figure 3C:
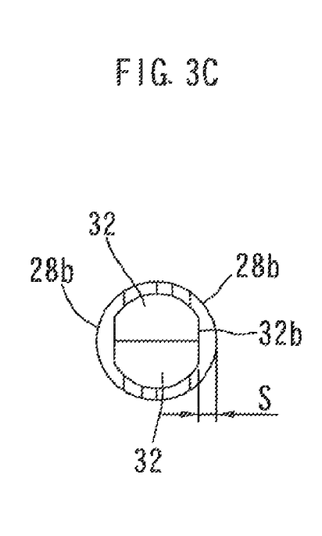

As shown in FIG. 3, an outer surface of the support piece 28b of the support member 28 is a cylindrical surface having a same radius as the base portion 28a. An outer surface of the gripping portion 32 of the clamp member 30 is a cylindrical surface having a smaller radius than the support piece 28b. Opposite side surfaces of the gripping portion 32 are chamfered to form flat surfaces 32b. Therefore, a dimension between the side surfaces of the gripping portion 32 in a direction of the shaft 33 is smaller than a dimension between the outer surfaces of the pair of support pieces 28b in the same direction. As a result, a step S is provided.

The link portions 31 of the pair of clamp members 30 extend rearward between the support pieces 28b. The pair of links 35 are located between the pair of support pieces 28b. One end portions of the links 35 are rotatably connected to rear end portions of the link portions 31 of the pair of clamp members 30 via shafts 36. The other end portions of the links 35 are rotatably connected to a distal end portion 25a of the wire 25 via a common shaft 37. The distal end portion 25a of the wire 25 is cut off to form a flat plate shape. The pair of links 35 are respectively disposed in opposite surfaces of the flat-plat shaped portion.

The link portions 31 of the pair of clamp members 30 and the pair of links 35 constitute a pantograph-type link mechanism 40 (link means).

A clip 50 will be described hereinafter with reference to FIG. 4. The clip 50 is composed of a single member of a spring material. The clip 50 includes a hinge portion 51 having a small thickness and a bent shape, a pair of connecting portions 52 continuous from opposite ends of the hinge portion 51 and having a general shape of letter S and a pair of clip portions 53 having shapes of flat plates extending elongately and linearly from the connecting portions 52. The pair of connecting portions 52 intersect with each other and the pair of clip portions 53 face each other.

Figure 4A:
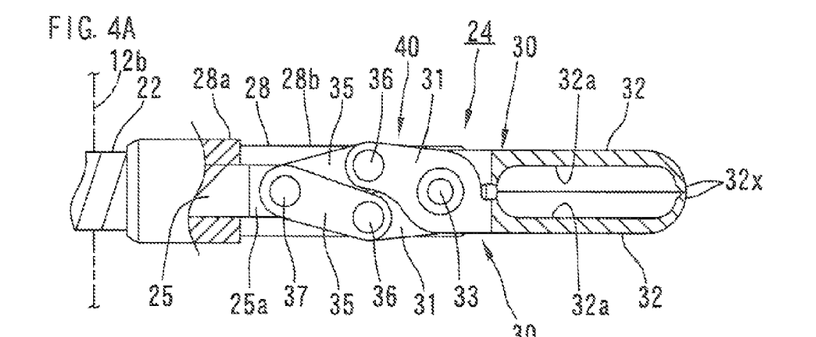
Figure 4B:
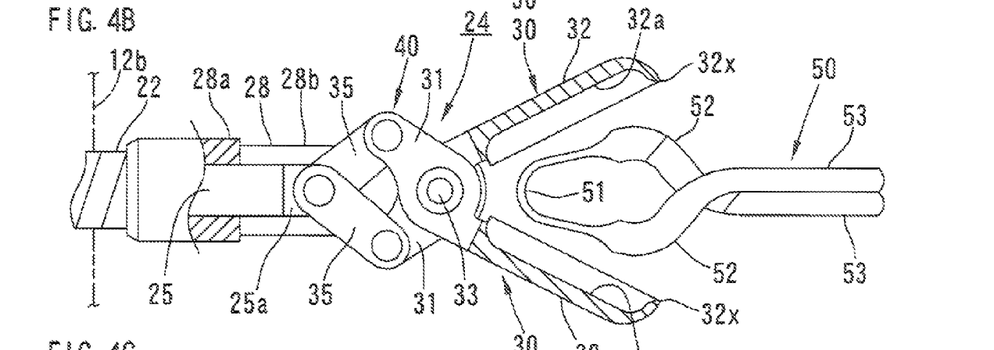

In a natural state, as shown in FIG. 4B, the hinge portion 51 tends to return to its original less curved condition, causing the clip portions 53 to be abutted against each other (closed condition). An elastic force of the hinge portion 51 is stronger than the elastic force of the spring 27 of the clip applier 20 mentioned earlier.

Operation of the clip applier 20 having the above mentioned construction will now be described. As a preliminary step, as shown in FIG. 1, the insertion tube 22 of the clip applier 20 is inserted from the guide tube 18 of the endoscope, and passed through the channel of the body 11 and the insertion portion 12, and the clamp mechanism 24 at the distal end of the insertion tube 22 is protruded out of the tip 12b of the insertion portion 12.

Amount of protrusion of the clamp mechanism 24 is adjusted such that the end surface of the tip 12b of the insertion portion 12 of the endoscope 10 is located in the vicinity of a rear end of the support member 28 as shown in FIG. 4, for example. After the adjustment of the amount of protrusion, the clamping dial 19 of the guide tube 18 is turned to apply a clamping force to the hard portion 22a of the insertion tube 22 of the clip applier 20. This locks the movement of the hard portion 22a, thereby locking the movement of the clip applier 20 with respect to the endoscope 10.

When the clip applier 20 is fixed to the endoscope 10 as mentioned above, the applier body 21 maintains a stable posture with respect to the endoscope 10 since the clamped portion is the hard portion 22a. This eliminates the necessity for an operator or an assistant to hold the applier body 21.

The observation window of the endoscope is located in a position offset with respect to the clamp mechanism 24 in a vertical direction in FIG. 3B (position offset in a direction orthogonal to the drawings in FIG. 4). The clip applier 20 is positioned with a posture that permits the pair of clamp members 30 to be seen in the left and right when viewed from the observation window.

Since the wire 25 is pulled by the spring 27, the shaft 37 is in a retracted position and the gripping portions 32 of the clamp members 30 are in abutment with each other in a closed condition as shown in FIG. 4A.

Before or after adjusting the amount of protrusion and the posture of the clamp mechanism 24, the operator inserts the thumb through the ring portion 21a and holds the operation member 23 with the index finger and the middle finger to move the operation member 23 forward (move the operation member 23 in a direction away from the ring portion 21a). This causes the wire 25 to move forward against the spring 27 and causes the shaft 37 to move forward as shown in FIG. 4B. As a result, the pair of gripping portions 32 of the clamp members 30 are opened via the link mechanism 40. In this open condition, the hinge portion 51 and the connecting portions 52 of the clip 50 are inserted between the pair of the gripping portions 32.

Figure 4C:
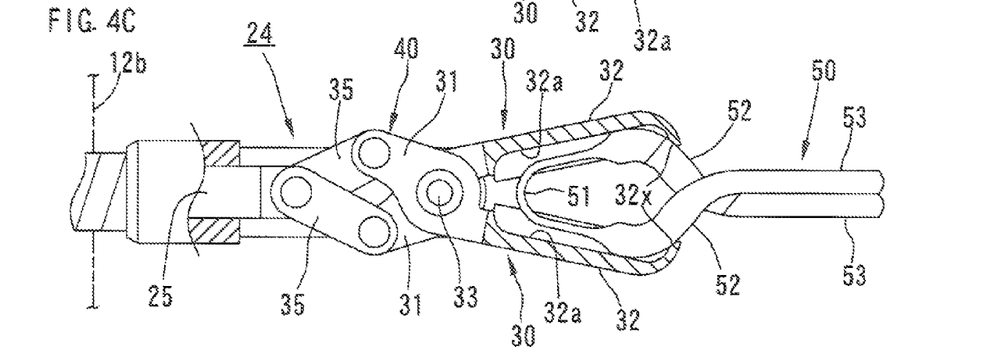

When the operating force to the operation member 23 is released, as shown in FIG. 4C, the wire 25 is retraced by the force of the spring 27, thereby causing the clamp members 30 to rotate in a closing direction. As a result, the pair of connecting portions 52 of the clip 50 are respectively received in the receiving grooves 32a of the pair of clamp members 30, thereby the clip 50 is held with the clamp members 30 by the force of the spring 27.

Since an inner dimension of the receiving grooves 32a in a width direction (direction orthogonal to the drawing in FIG. 4) and a dimension of the connecting portions 52 of the clip 50 in the same direction are equal, the clip 50 will not rattle in the same direction.

Since the distal edge portions 32x of the gripping portions 32 are abutted against inclined surfaces of the connecting portions 52 of the clip 50 facing the clip portions 53 side, the clip 50 will not fall off. Since portions of the connecting portions 52 in the vicinity of the hinge portion 51 are abutted against flat bottom surfaces of the receiving grooves 32a of the gripping portions 32, the clip 50 will not move rearwardly. In this way, the clip 50 is stably held without rattle in a front and rear direction.

In the above-mentioned manner, an assembly is obtained in which the clip applier 20 holding the clip 50 is mounted to the endoscope 10. In this condition, the operator inserts the insertion portion 12 of the endoscope 10 from an opening formed in the cranium of the patient and moves the distal end of the insertion portion 12 forward to the affected area such as an aneurysm, controllably bending the bendable portion 12a by operating the operation portion 13 while monitoring the TV screen.

Figure 4D:
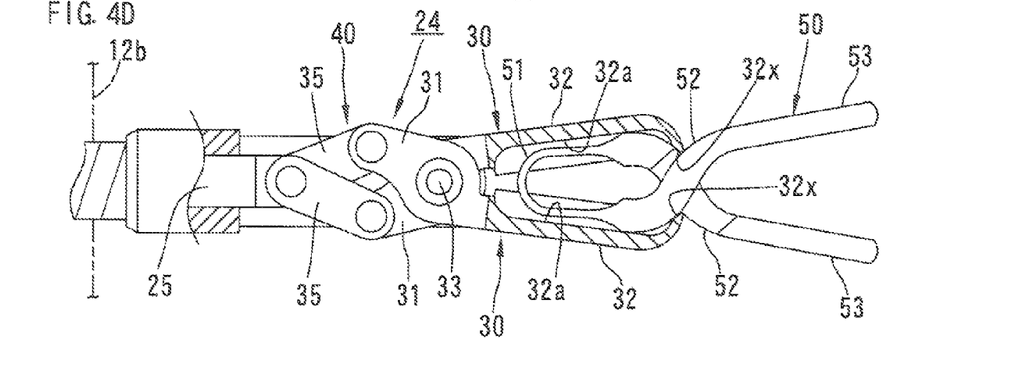

When the distal end of the insertion portion 12 reaches the vicinity of the aneurysm, the operation member 23 is retracted (moved toward the ring portion 21a) to pull the wire 25. This causes the gripping portions 32 of the clamp members 30 to press the connecting portions 52 against the elastic force of the hinge portion 51 of the clip 50 as shown in FIG. 4D, thereby causing the pair of clip portions 53 to be opened. As shown in FIG. 4D, when the distal edge portion 32x of each of the gripping portions 32 is abutted against not only the inclined surface of the corresponding connecting portion 52 but also the other connecting portion 52, the pair of the clip portions 53 cannot be opened any further, being in the maximum open condition.

After the endoscope 10 is positionally adjusted such that a neck of the aneurysm, where it bulges from the blood vessel, is located between the clip portions 53 in the open condition, the operating force of the operation member 23 in a retracting direction is released. This causes the clip portions 53 to be moved in a closing direction by the elastic force of the hinge portion 51, thus the clip portions 53 can strongly clip and ligate the neck.

After that, the operation member 23 is moved forward to widely open the clamp members 30 as shown in FIG. 4B. The distal end of the insertion portion 12 is retracted from the affected area to remove the clamp members 30 form the clip 50.

As mentioned above, the clip applier 20 is positioned such that the pair of clip portions 53 of the clip 50 can be seen in the left and right in the field of view of the endoscope 10. Since the steps S are formed between the side surfaces of the gripping portions 32 of the clamp members 30 and side surfaces of the support pieces 28b of the support member 28, the clip 50 can be clearly seen without being obstructed by the gripping portions 32 of the clamp members 30. This prevents injuries to the brain caused by the clip 50 during the forward movement of the endoscope as well as facilitating application of the clip 50 to the affected area.

In this embodiment, since the distal edge portion 32x of the gripping portion 32 serves as one of the pressing portions for pressing the clip 50 (the other of the pressing portions is the bottom surface of the receiving groove 32a), the connecting portion 52 can be pressed at a point spaced away from the hinge portion 51. As a result, the clip 50 can be opened with a relatively small force.

Figure 5A:
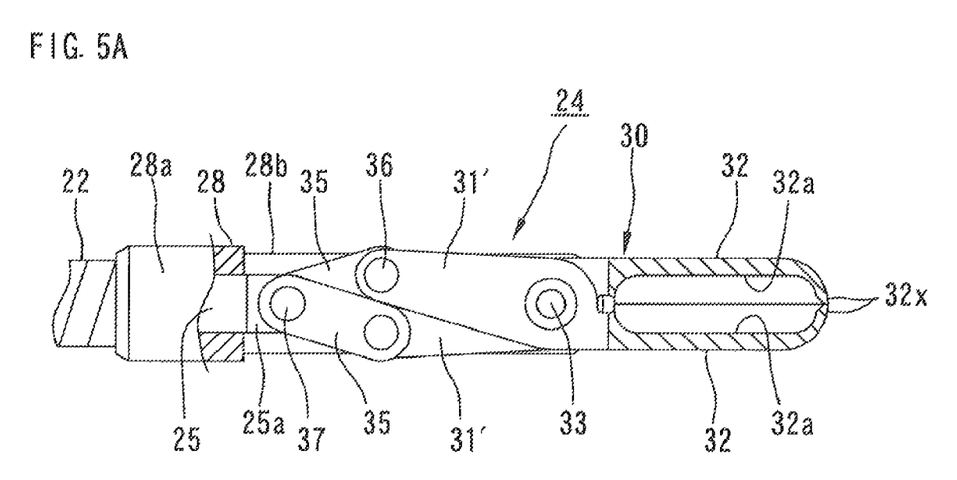
Figure 5B:
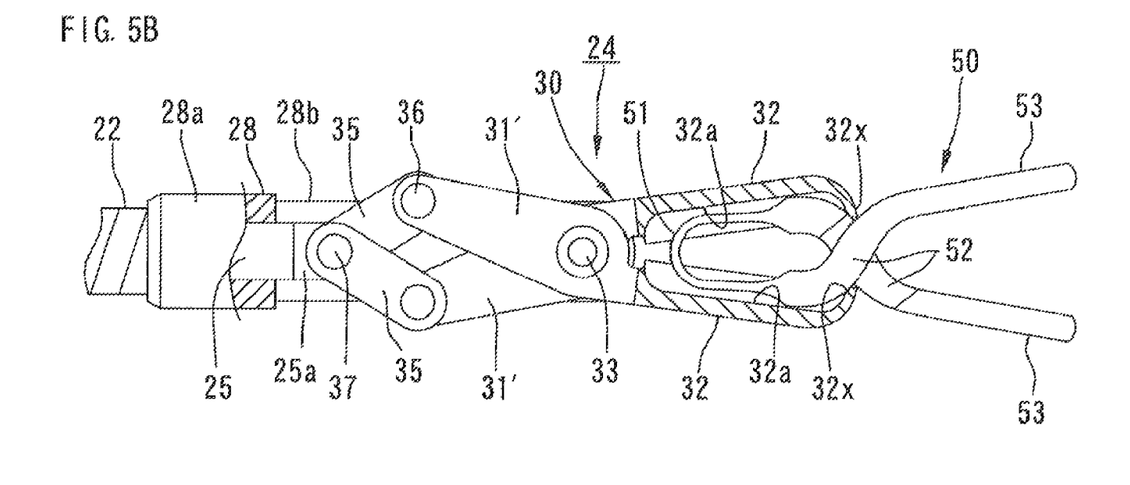

FIG. 5 shows the clamp mechanism 24 of the clip applier according to a second embodiment of the present invention. In the description of the second embodiment, components corresponding to those in the first embodiment are designated by the same numerals and description thereof will be omitted. In the second embodiment, link portions 31' of the clamp members 30 are longer than the link portions 31 of the first embodiment and longer than the links 35. This enables the clip 50 to be opened with a smaller force than in the first embodiment.

Although described with respect to preferred embodiments, various modifications may be made. For example, the clip portions of the clip can be of various configurations depending on the purposes, without being limited to the above-described embodiments.

The insertion tube of the clip applier may be flexible throughout its length.

Only one of the clamp members forming the pair may be rotatably supported by the support member while the other may be fixed to or integrally formed with the support member.

In this case, of the link portions 31 (31') and the links 35 of the first and the second embodiments, only one each is required.

The applier body and the operation member may have pistol-like configurations.

Although each of the connecting portions of the clip is supported at two points, one in the distal edge portion of the gripping portion and the other in the bottom surface of the receiving groove in the embodiments mentioned above, the connecting portion of the clip may be abutted against only the distal edge portion of the gripping portion. In this case, a stopper to be abutted against the hinge portion is required to be disposed at the support member or the clamp members to prevent the clip from retracting.

The clip applier may be inserted in the endoscope after a distal end of the insertion portion of the endoscope has reached the affected area. In this case, the diameter of the channel of the endoscope should be greater or the dimensions of the clip should be smaller than those in the above mentioned embodiments.

The clip applier of the present invention is most suitable for use in the brain surgery but may be applied to surgeries of other parts of the body.

What is claimed is:

1. A clip applier for applying a clip to an affected area to ligate the affected area, the clip integrally comprising a hinge portion, a pair of clip portions and a pair of connecting portions respectively connecting opposite ends of the hinge portion to the pair of clip portions, the connecting portions intersecting with each other, the pair of clip portions being biased to be closed by an elastic force of the hinge portion, wherein the clip applier comprises:
an applier body;
an insertion tube extending from the applier body and inserted through a channel of an endoscope;
a clamp mechanism disposed at a distal end of the insertion tube;
an operation member disposed on the applier body; and
a wire passing through the insertion tube to connect the clamp mechanism and the operation member,
the clamp mechanism comprising a support member fixed at the distal end of the insertion tube and a pair of clamp members rotatably supported by the support member,
the pair of clamp members respectively comprising gripping portions protruded from the support member, the gripping portions respectively comprising receiving grooves in surfaces of the gripping portions facing each other, the pair of connecting portions of the clip respectively received in the receiving grooves of the gripping portions of the clamp members and the clip portions of the clip protruded from the gripping portions in a condition where the clip is held by the clamp members wherein the pair of clamp members intersect with each other, the clamp members being supported by the support member at the intersecting portions of the clamp members such that the clamp members are rotatable about a common shaft, the clamp members respectively comprising link portions integrally formed with the gripping portions, the clamp mechanism further comprising a pair of links, one ends of the links being respectively rotatably connected to the link portions of the clamp members, the other ends of the links being rotatably connected to the distal end of the wire, the link portions of the pair of clamp members and the pair of links constituting a pantograph-type link mechanism, the pair of clamp members being connected to the operation member via the link mechanism and the wire, when the wire is pulled by operating the operation member, the the pair of clamp members being rotated via the link mechanism against the elastic force of the hinge portion of the clip, thereby causing the gripping portions of the pair of clamp members to press the pair of connecting portions of the clip, thereby opening the clip portions.

2. A clip applier according to claim 1, wherein the insertion tube comprises a hard portion to be rigidly joined with the applier body and a flexible portion having a greater length than the hard portion.

3. A clip applier according to claim 1, wherein distal edge portions of the gripping portions of the clamp members serve as pressing portions for pressing the connecting portions of the clip.

4. A clip applier according to claim 3, wherein each of the pair of clamp members is abutted against the connecting portion of the clip at two points when the clamp members hold the clip, one point being in the distal edge portion of the gripping portion and the other point being in a bottom surface of the receiving groove.

5. A clip applier according to claim 1, wherein a length of the link portions of the pair of clamp members is greater than a length of the pair of links.

6. A clip applier according to claim 1, wherein the support member comprises a base portion fixed to the distal end of the insertion tube and a pair of support pieces extending from the base portion, the link portions of the clamp members and the links being received between the support pieces, the clamp members rotatably supported at distal end portions of the support pieces,
a dimension between opposite side surfaces of the gripping portions of each of the clamp members in a direction of a rotation axis being smaller than a dimension between outer surfaces of the pair of support pieces in the same direction, thereby forming steps between the outer surfaces of the support pieces and the side surfaces of the gripping portions of the clamp members.

7. A clip applier according to claim 1, wherein a spring is disposed in the applier body, the spring biasing the wire in a direction to pull the wire, an elastic force of the spring being smaller than the elastic force of the hinge portion of the clip.

* * * * *